United States Patent [19]

Eberle

[11] Patent Number: 5,284,826
[45] Date of Patent: Feb. 8, 1994

[54] 0-HYDROXYETHYL AND ACYLOXYETHYL DERIVATIVES OF [SER]⁸ CYCLOSPORINS

[75] Inventor: Marcel K. Eberle, Riehen, Switzerland

[73] Assignee: Sandoz Ltd., Basel, Switzerland

[21] Appl. No.: 936,695

[22] Filed: Aug. 27, 1992

Related U.S. Application Data

[63] Continuation of Ser. No. 556,603, Jul. 20, 1990, abandoned.

[30] Foreign Application Priority Data

Jul. 24, 1989 [GB] United Kingdom ............... 8916901

[51] Int. Cl.⁵ .................. A61K 37/02; C07K 7/64
[52] U.S. Cl. .................... 514/11; 530/321; 530/317; 514/863; 514/885; 514/886; 514/880; 514/826
[58] Field of Search ............... 530/317, 321; 514/11, 514/9, 863, 885, 886, 880, 826, 908

[56] References Cited

U.S. PATENT DOCUMENTS 4,384,996 5/1983 Bollinger et al. ............... 530/321

OTHER PUBLICATIONS

Rudinger, Peptide Hormones, Parsons, J Park Press, Baltimore, pp. 1-7 (1976).
Twentyman et al., Br. J. Cancer vol. 56, pp. 55-57 (1987).

*Primary Examiner*—Y. Christina Chan
*Attorney, Agent, or Firm*—Robert S. Honor; Melvyn M. Kassenoff; Thomas O. McGovern

[57] ABSTRACT

Hydroxy-substituted [(D)Ser]⁸-Ciclosporin derivatives, particularly [O-(2-hydroxyethyl)(D)Ser]⁸-Ciclosporin, have advantageous pharmacological properties and are useful as immunosuppressants, for example in the treatment of transplant rejection and autoimmune diseases.

12 Claims, No Drawings

O-HYDROXYETHYL AND ACYLOXYETHYL DERIVATIVES OF [SER]⁸ CYCLOSPORINS

This is a continuation of application Ser. No. 07/556,603, filed Jul. 20, 1990 now abandoned.

The present invention relates to novel cyclosporins, their use as pharmaceuticals and pharmaceutical compositions comprising them, as well as to processes for their production.

The cyclosporins comprise a class of structurally distinctive, cyclic, poly-N-methylated undecapeptides, commonly possessing pharmacological, in particular immunosuppressive, anti-inflammatory and/or antiparasitic activity. The first of the cyclosporins to be isolated was the naturally occurring fungal metabolite Ciclosporin or Cyclosporine, also known as cyclosporin A and commercially available under the Registered Trademark SANDIMMUN$^R$ or SANDIMMUNE$^R$. Ciclosporin is the cyclosporin of formula A.

duction of cyclosporins developed by r. Wenger—see e.g. Traber et al. 1, Traber et al, 2 and Kobel et al., loc. cit.; U.S. Pat. Nos. 4,108,985, 4,220,641, 4,288,431, 4,554,351, 4,396,542 and 4,798,823 European Patent Publications Nos. 34,567A, 56,782A, 300,784A and 300,785A; International Patent Publication No WO 86/02080 and UK Patent Publications Nos. 2,206,119 and 2,207,678; Wenger 1, Transpl. Proc., 15 Suppl. 1:2230 (1983); Wenger 2., Angew. Chem. Int. Ed. 24 77 (1985) and Wenger 3., Progress in the Chemistry of Organic Natural Products, 50, 123 (1986).

The class comprised by the cyclosporins is thus now very large indeed and includes, for example, [Thr]²-, [Val]²-, [Nva]²- and [Nva]²-[Nva]⁵-Ciclosporin (also known as cyclosporins C, D, G and M respectively), [3-O-acetyl-MeBmt]¹-Ciclosporin (also known as cyclosporin A acetate), [Dihydro-MeBmt]¹-[Val]²-Ciclosporin (also known as dihydro-cyclosporin D), [(D)Ser]⁸-Ciclosporin, [MeIle]¹¹-Ciclosporin, [(D)Me-Val]¹¹-Ciclosporin (also known as cyclosporin H),

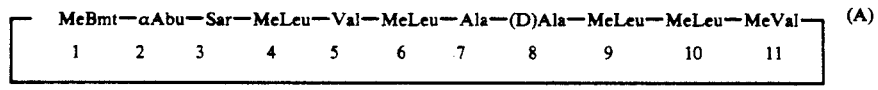  (A)

where MeBmt represents the N-methyl-(4R)-4-but-2E-en-1-yl-4-methyl-(L)threonyl residue of formula B

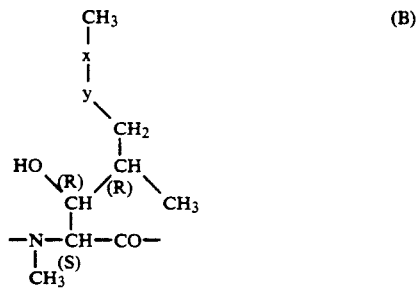  (B)

in which -x-y- is —CH═CH— (trans).

Since the original discovery of Ciclosporin, a wide variety of naturally occurring cyclosporins have been isolated and identified and many further non-natural cyclosporins have been prepared by total- or semi-synthetic means or by the application of modified culture techniques. The class comprised by the cyclosporins is thus now substantial and includes, for example, the naturally occurring cyclosporins A through Z [cf. Traber et al; 1, Helv. Chim. Acta, 60, 1247-1255 (1977); Traber et al; 2, Helv. Chim. Acta, 65, 1655-1667 (1982); Kobel et al, Europ. J. Applied Microbiology and Biotechnology, 14, 273-240 (1982); and von Wartburg et al, Progress in Allergy, 38, 28-45, (1986)], as well as various non-natural cyclosporin derivatives and artificial or synthetic cyclosporins including dihydro-cyclosporins [in which the moiety -x-y- of the MeBmt residue (formula B above) is saturated to give -x-y-═—CH₂—CH₂—]; derivatised cyclosporins (e.g. in which the 3'-O-atom of the MeBmt residue is acylated or a further substituent is introduced at the α-carbon atom of the sarcosyl residue at the 3-position); cyclosporins in which the MeBmt residue is present in isomeric form (e.g. in which the configuration across positions 6' and 7' of the MeBmt residue is cis rather than trans); and cyclosporins in which variant amino acids are incorporated at specific positions within the peptide sequence, e.g. employing the total synthetic method for the pro-

[MeAla]⁶-Ciclosporin, [(D)Pro]³-Ciclosporin and so on.

In accordance with conventional nomenclature for cyclosporins, these are defined throughout the present specification and claims by reference to the structure of Ciclosporin (i.e. Cyclosporin A). This is done by first indicating those residues in the molecule which differ from those present in Ciclosporin and then applying the term "Ciclosporin" to characterise the remaining residues which are identical to those present in Ciclosporin. At the same time the prefix "dihydro" is employed to designate cyclosporins wherein the MeBmt residue is hydrogenated (dihydro-MeBmt) i.e. where -x-y- in formula B is —CH₂—CH₂—. Thus [Thr]²-Ciclosporine is the cyclosporin having the sequence shown in Formula A but in which αAbu at the 2-position is replaced by Thr, and [Dihydro-MeBmt]¹-[Val]²-Ciclosporin is the cyclosporin having the sequence shown in Formula A but in which the MeBmt residue at position 1 is hydrogenated and aAbu at the 2-position is replaced by Val.

In addition, amino acid residues referred to by abbreviation, e.g. Ala, MeVal, aAbu etc. are, in accordance with conventional practice, to be understood as having the (L)-configuration unless otherwise indicated, e.g. as in the case of "(D)Ala". Residue abbreviations preceded by "Me" as in the case of "MeLeu", represent α-N-methylated residues. Individual residues of the cyclosporin molecule are numbered, as in the art, clockwise and starting with the residue MeBmt or dihydro-MeBmt in position 1. The same numerical sequence is employed throughout the present specification and claims.

In accordance with the present invention it has now been found that cyclosporins in which the residue at the 8-position is a hydroxy substituted (D)serine residue exhibit particularly interesting pharmaceutical properties.

The present invention thus provides a cyclosporin in which the residue at the 8-position is a residue of formula I

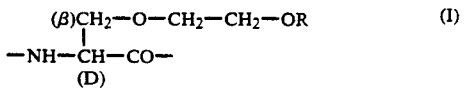

$$\begin{array}{c} (\beta)CH_2-O-CH_2-CH_2-OR \\ | \\ -NH-CH-CO- \\ (D) \end{array} \quad (I)$$

where R is hydrogen or acyl.

Preferably R is hydrogen. When R is acyl, this may represent a physiologically hydrolysable and acceptable acyl residue, that is a residue which is cleavable under physiological conditions to yield an acid (ROH) which is itself physiologically tolerable at dosages to be administered. Suitable acyl groups R include ($C_{1-4}$alkyl)carbonyl, for example acetyl, and monocyclic arylcarbonyl, for example benzoyl and salicyl.

Preferred cyclosporins in accordance with the present invention are those of formula II

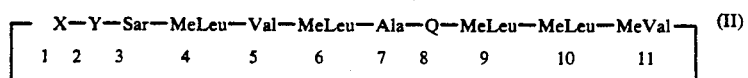

$$\left[\begin{array}{cccccccccccc} X-Y-Sar-MeLeu-Val-MeLeu-Ala-Q-MeLeu-MeLeu-MeVal \\ 1 \quad 2 \quad 3 \quad 4 \quad 5 \quad 6 \quad 7 \quad 8 \quad 9 \quad 10 \quad 11 \end{array}\right] \quad (II)$$

in which
X is MeBmt or dihydro-MeBmt,
Y is αAbu, Val, Thr or Nva, and
Q is a residue of formula I as described above.

The most preferred compound of the invention is [O-(2-hydroxyethyl)(D)Ser]$^8$-Ciclosporin, that is, the cyclosporin of Formula II in which X is MeBmt, Y is αAbu, and Q is a residue of formula I in which R is hydrogen.

The present invention also provides a process for the production of cyclosporins of the present invention, e.g. for the production of cyclosporins of formula II, which process comprises:

i) for the production of a cyclosporin (e.g. of formula II) wherein the residue at the 8-position (Q in formula II) is a residue of formula I as defined above in which R is hydrogen, reducing a corresponding cyclosporin wherein the residue at the 8-position is a residue of formula III

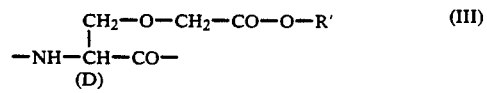

$$\begin{array}{c} CH_2-O-CH_2-CO-O-R' \\ | \\ -NH-CH-CO- \\ (D) \end{array} \quad (III)$$

where R' is $C_{1-3}$ alkyl, for example reducing a cyclosporin of formula IV

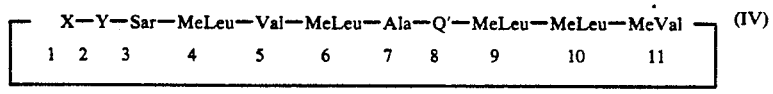

$$\left[\begin{array}{cccccccccccc} X-Y-Sar-MeLeu-Val-MeLeu-Ala-Q'-MeLeu-MeLeu-MeVal \\ 1 \quad 2 \quad 3 \quad 4 \quad 5 \quad 6 \quad 7 \quad 8 \quad 9 \quad 10 \quad 11 \end{array}\right] \quad (IV)$$

wherein X and Y have the meanings given for formula II and Q' is a residue of formula III as defined above; or ii) for the production of a cyclosporin, e.g. of formula II, in which the residue at the 8-position (Q in formula II) is a residue of formula I as defined above in which R is acyl, esterifying the corresponding cyclosporin in which R is hydrogen.

Reduction in accordance with process variant i) may be carried out employing conventional methods for reducing ester groups to hydroxymethyl groups, for example by treatment with lithium borohydride under an inert atmosphere, in an appropriate solvent or diluent at ambient or moderately elevated temperature. The lithium borohydride may conveniently be replaced by sodium borohydride in the presence of a lithium halide.

Esterification in accordance with process variant ii) may be carried out in accordance with conventional procedures, for example by reaction with acid halides or anhydrides, e.g. ($C_{1-4}$alkyl)carbonyl halides, in the presence of an acid binding agent.

The starting materials for process variant i) may be prepared in accordance with the following reaction method (for convenience, only the transformed residue at the 8-position is indicated):

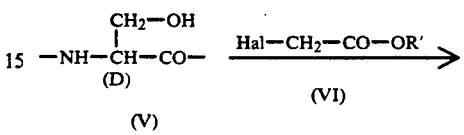

$$\begin{array}{c} CH_2-OH \\ | \\ -NH-CH-CO- \\ (D) \end{array} \xrightarrow{Hal-CH_2-CO-OR'}$$

$$(V) \qquad\qquad (VI)$$

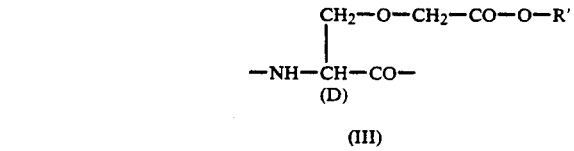

$$\begin{array}{c} CH_2-O-CH_2-CO-O-R' \\ | \\ -NH-CH-CO- \\ (D) \end{array}$$

$$(III)$$

in which R' is as defined above, and is preferably $C_3$ alkyl, particularly isopropyl; and Hal is bromine or iodine. The reaction is suitably performed in accordance with or analogously to the general procedures of Example 1 below.

Cyclosporins in which the residue at the 8-position is of formula V (that is, (D)Ser), for example [(D)Ser]$^8$-Ciclosporin, are known and are described together with processes for their production e.g. in European Patent Publication 56 782 A and British Patent Specification 2 155 936 A.

Cyclosporins according to the invention may exist in the solid state in amorphous form or in one or more crystalline forms. For example, the compound of Example 2 below exists in amorphous form or in at least three crystalline forms, distinguishable by X-ray diffraction and designated the A, B and C modifications. Of these, the B form, a hydrate obtainable by recrystallization from acetone/water, is the most stable and therefore the preferred form.

Cyclosporins in which the residue at the 8-position is a residue of formula III as defined above are new and also form part of the present invention.

The following examples, in which all temperatures are in degrees centigrade, illustrate the invention.

EXAMPLE 1

[O-(isopropyloxycarbonylmethyl)(D)Ser]$^8$-Ciclosporin

[(D)Ser]$^8$-Ciclosporin (21.89 g of 88.7% pure material from a chromatography fraction of a fermentation broth, =19.42 g, 15.93 mMol, of 100% material) is dissolved in toluene (160 ml) and tetra-N-butylammonium bromide (1.03 g, 3.2 mMol) is added. To the solution is added bromoacetic acid isopropyl ester (14.41 g, 79.7 mMol) over 5 min. at 20°-25°, and the mixture is stirred for 30 min. at 20°-25° while 30% aqueous sodium hydroxide solution (53.1 g, =15.93 g pure NaOH, 398 mMol) is added dropwise. After stirring for a further 30 min. at 20°-25°, the aqueous phase is separated and extracted with toluene (63 ml). The toluene phases are combined and washed with saturated aqueous ammonium chloride solution (80 ml) then with water (48 ml), then dried over aluminium oxide, filtered and evaporated to give a solid yellow foam (22–32 g).

The residue is taken up in toluene (31 ml), and the solution warmed to 65°-68°. To the warm solution is added dropwise over 90 min. 125 ml n-hexane, and the mixture is cooled to 20°-25° over 4 hr, stirred 10 hr at room temperature and finally cooled over 3 hr to 0°-3° and stirred at this temperature for 2 hr. The resulting crystals are filtered off, washed with ice-cold toluene/hexane 1:4 (42 ml) and dried at 60° under vacuum to give the title product (19.2 g) as beige crystals of purity 87.9% (by high-pressure liquid chromatography, HPLC) which can be used in the next step without further purification.

Alternatively, further recrystallisation gives the pure title product as white crystals, m.p. 168°-170°; $[\alpha]_D^{20} = -162.4°$ (methanol, c=0.37).

EXAMPLE 2

[O-(2-hydroxyethyl)(D)Ser]$^8$-Ciclosporin

Step a): Crude Product

The crude product of Example 1 (14.1 g 87.9% purity=12.39 g, 9.4 mMol, of pure material) is dissolved in absolute ethanol (315 ml) and warmed to 30°-35° under a nitrogen atmosphere. To the solution is added in 7 portions over 6 hr lithium borohydride (total of 1.29 g 95% purity=1.225 g, 56.3 mMol, 6 equivalents, of pure material). After each addition a slightly exothermic reaction occurs, with evolution of gas. The resulting beige suspension is stirred for 14 hr at 30°-35°, then cooled to 20°-25° and treated with 23 ml of a 20% aqueous solution of acetic acid. The clear pale yellow solution (pH 5-6) is stirred for 30 min. then evaporated to give approx. 30 ml of an oily residue.

The residue is partitioned between isopropyl acetate (IPA) (130 ml) and water (80 ml) and the aqueous phase re-extracted with IPA (40 ml). The combined IPA layers are washed with 25 ml saturated aqueous sodium bicarbonate solution, then with 30 ml water, and the solvent evaporated to give the crude title product as a beige foam (13.44 g, purity 81.8% by HPLC).

Step b): Purification

The crude product of step a) (36.2 g) is dissolved in methyl isobutyl ketone (MIBK) saturated with water, and chromatographed on KIESELGEL 0.04–0.063 mm (885 g), column dimensions 460×70 mm diameter, using water-saturated MIBK as eluant. After an initial run-off of 2 lit., fractions containing material of >95% purity as measured by HPLC are collected giving approx. 11.5 lit. of solution, which is evaporated to dryness under vacuum to give 24.3 g of the amorphous title product as a beige foam; purity by HPLC=95.2%.

The solid product is dissolved in acetone (40 ml) and the pale yellow solution filtered through a sintered glass funnel which is then rinsed with acetone (21 ml). To the combined acetone solution water (61 ml) is added dropwise over 90 min., with the appearance of crystals. The fine suspension is stirred for 16 hr at room temperature then cooled to 0°-3° over 1 hr, stirred for a further 4 hr then filtered, washed with ice-cold acetone/water 1:1, and the damp crystals dried 14 hr at 60° under partial vacuum to give the pure title product (20.76 g) as white crystals of the B modification, purity by HPLC 98%, m.p. approx. 130° (dec.).

Further recrystallisations from acetone/water give material of even higher purity.

From the amorphous material obtained as described above, crystal modification A is obtained by recrystallization from polyethylene/glycol/water; and crystal modification C is obtained by recrystallization from ethanol/water or by ultrasonic treatment of a suspension of the amorphous form in ethanol/water. Melting points: modification A: 148° C. approx.; modification C: 120° C. approx.

EXAMPLE 3

[O-(2-Acetyloxyethyl)(D)Ser]$^8$-Ciclosporin

The product of step a) of Example 2 (600 mg, 0.47 mMol) is dissolved in pyridine (30 ml) and mixed with acetic anhydride (30 ml). The mixture is kept at room temperature for 2.5 hr., after which the pyridine and excess acetic anhydride are evaporated under reduced pressure and the residue chromatographed on silica gel with ether/ethyl acetate 4:1 as eluent to yield the title product (430 mg).

$[\alpha]_D^{20} = -175.8 (c=0.25$ in methanol).

Cyclosporins comprising a residue of formula I as hereinbefore defined at the 8-position (hereinafter "Product Cyclosporins"), in particular cyclosporins of formula II as hereinbefore defined, possess pharmaceutical utility as may be demonstrated, for example, in the following test methods:

1. Localised Graft-versus-Host (GvH) Reaction in the rat [Ford et al., TRANSPL. PROC. 10 (1970) 258].

Spleen cells ($1 \times 10^7$) from 6 week old female Wistar/Furth (WF) rats are injected subcutaneously on day 0 into the left hind-paw of female (F344×WF)F$_1$ rats weighing about 100 g. Animals are treated for 4 consecutive days and the popliteal lymph nodes are removed and weighed on day 7. The difference in weight betwen the two lymph nodes is taken as the parameter for evaluating the reaction.

Product Cyclosporins inhibit GvH reaction in the above test method on administration 4× at dosages of from about 10 to about 30 mg/kg p.o., or about 1.5 to 5 mg/kg s.c..

2. Kidney Allograft Reaction in the Rat

One kidney from a female Fisher 344 rat is transplanted onto the renal vessel of a unilaterally (left side) nephrectomised WF recipient rat using an end-to-end anastomosis. Ureteric anastamosis is also end-to-end. Treatment commences on the day of transplantation and is continued for 14 days. A contralateral nephrectomy is done seven days after transplantation, leaving the recipient relying on the performance of the donor kidney. Survival of the graft is taken as the parameter for a functional graft.

Product cyclosporins are effective in maintaining graft survival in the above test method on administration at dosages of from about 2 to about 5 mg/kg/day p.o..

3. Experimentally Induced Allergic Encephalomyelitis (EAE) in the Rat [Levine et al., AM. J. PATH. 47 (1965) 61; McFarlin et al, J. IMMUNOL. 113 (1974)

712; Borel, TRANSPLANT & CLIN. IMMUNOL. 13 (1981) 3].

Male Wistar rats are injected in the hind paws with a mixture of bovine spinal cord and complete Freund's adjuvant. Symptoms of the disease (paralysis of the tail and both hind legs) usually develop within 16 days. The number of diseased animals as well as the time of onset of the disease are recorded.

On adminstration at dosages of from about 12.5 to about 25 mg/kg/day p.o.. Product Cyclosporins inhibit disease onset in the above test model.

4. Freund's Adjuvant Arthritis [Winter & Nuss, ARTHRITIS AND RHEUMATISM 9 (1966) 394; Billingham & Davies, HANDBOOK OF EXPERIMENTAL PHARMACOL (Vane & Ferreira Eds, Springer-Verlag, Berlin,) 50/II, (1979) 108–144]

OFA and Wistar rats (male or female, 150 g body weight) are injected i.c. at the base of the tail or in the hind paw with 0.1 ml of mineral oil containing 0.6 mg of lyophilised heat-killed Mycobacterium smegmatis. In the developing arthritis model, treatment is started immediately after the injection of the adjuvant (days 1–18); in the established arthritis model treatment is started on day 14, when the secondary inflammation is well developed (days 14–20). At the end of the experiment, the swelling of the joints is measured by means of a micro-caliper.

Product Cyclosporins are effective in preventing or inhibiting disease progression in both developing and established test models on administration at dosages of from about 3 to about 20 mg/kg/day p.o..

Product Cyclosporins also exhibit favourable toxicity, e.g. hepatotoxic and/or nephrotoxic, profiles as compared with known cyclosporins, for example Ciclosporin, as may be demonstrated by determination of their influence on relevant parameters, e.g. blood creatinine; glomerular filtration rate; urea, bilirubin and bile acid levels, following long term administration to rats at immunosuppressively effective dosage rates. Product Cyclosporins are thus characterised by an improved therapeutic ratio as compared with known cyclosporins.

Product Cyclosporins are therefore useful as pharmaceuticals, e.g. as immunosuppressive as well as anti-inflammatory agents.

Product Cyclosporins are in particular useful for the prevention of organ or tissue transplant rejection, e.g. for the treatment of recipients of heart, lung, combined heart-lung, liver, kidney, pancreatic, skin or corneal transplants. They are also indicated for the prevention of graft-versus-host disease, such as following bone marrow transplants.

Product Cyclosporins are also useful for the treatment of autoimmune disease and of inflammatory conditions, in particular inflammatory conditions with an aetiology including an autoimmune component such as arthritis (for example rheumatoid arthritis, arthritis chronica progrediente and arthritis deformans) and rheumatic diseases. Specific auto-immune diseases for which product Cyclosporins may be employed include autoimmune haematological disorders (including e.g. haemolytic anaemia, aplastic anaemia, pure red cell anaemia and idiopathic thrombocytopenia), systemic lupus erythematosus, polychondritis, sclerodoma, Wegener granulamatosis, dermatomyositis, chronic active hepatitis, myasthenia gravis, psoriasis, Steven-Johnson syndrome, idiopathic sprue, autoimmune inflammatory bowel disease (including e.g. ulcerative colitis and Crohn's disease) endocrine ophthalmopathy, Graves disease, sarcoidosis, multiple sclerosis, primary billiary cirrhosis, juvenile diabetes (diabetes mellitus type I), uveitis (anterior and posterior), keratoconjunctivitis sicca and vernal keratoconjunctivitis, interstitial lung fibrosis, psoriatic arthritis and glomerulonephritis (with and without nephrotic syndrome, e.g. including idiopathic nephrotic syndrome or minimal change nephropathy).

Product Cyclosporins are further indicated for use in the treatment of other diseases or conditions for which cyclosporin, e.g. Ciclosporin, therapy is practiced or proposed, for example, for the treatment of alopecia/-the promotion of hair growth and for the treatment of asthma, e.g. on administration by inhalation. They are also indicated for use as anti-parasitic agents, in particular for the treatment of parasitic, e.g. protozoal, fungal or vermicular infection or invasion, for example in the treatment of filariasis, schistosomiasis, coccidiomycosis or plasmodial infection, e.g. malaria. They are yet further indicated for use in the reversal of induced resistance of malignancies to other chemotherapy, as well as the enhancement of wound healing.

For the above indications the appropriate dosage will, of course, vary depending, for example, on the particular Product Cyclosporin employed, the subject to be treated, the mode of administration and the nature and severity of the condition being treated. However, in general, satisfactory results in animals are obtained at daily dosages of from about 1 to about 10 mg/kg/day p.o. In larger mammals, for example humans, an indicated daily dosage is in the range of from about 50 to about 800 mg of Product Cyclosporin administered orally once or, more suitably, in divided dosages two to four times/day.

In organ transplantation in humans, an initial single oral dose of 10–15 mg/kg Product Cyclosporin 4–12 hours prior to surgery is indicated. This daily dose is maintained for one to two weeks post-operatively, before being gradually reduced in accordance with blood levels until a maintenance dose of about 2–6 mg/kg/day is reached. When Product Cyclosporins are given along with other immunosuppressants (e.g. with corticosteroids as part of a triple or quadruple drug therapy) lower doses (e.g. 1 mg/kg/day i.v.; 6 mg/kg/day oral initially) may be used.

Product Cyclosporins may be administered by any conventional route, in particular enterally, e.g. orally, for example in the form of solutions for drinking, tablets or capsules or parenterally, for example in the form of injectible solutions or suspensions. Normally for systemic administration oral dosage forms are preferred, although for some conditions, for example for prevention of rejection of liver transplants, an intravenously injectable form is desirable. Product Cyclosporins may also be administered topically or dermally, e.g. in the form of a dermal cream or gel or like preparation or, for the purposes of application to the eye, in the form of an occular cream, gel or eye-drop preparation. Suitable unit dosage forms for oral administration comprise e.g. from 25 to 200 mg Product Cyclosporin per dosage.

Preferred galenic formulations for Product Cyclosporins include those based on microemulsions as described in British Patent Application 2 222 770A, which include topical as well as oral forms; also oral and injectable forms obtained from solid solutions comprising a fatty acid saccharide monoester, e.g. saccharose monolaurate, as described in British Patent Application 2 209 671A.

Examples of particularly preferred formulations suitable for filling soft gelatine capsules for oral administration include:

| Formulation Example A: | |
|---|---|
| Product of Ex. 2 | 50.0 mg |
| GLYCOFUROL 75 | 180.0 mg |
| MIGLYOL 812 | 90.0 mg |
| CREMOPHOR RH 40 | 180.0 mg |
| alpha-Tocopherol | 0.5 mg |
| Formulation Example B: | |
| Product of Ex. 2 | 100.0 mg |
| Tetraglycol | 20.0 mg |
| CAPTEX 800 | 20.0 mg |
| NIKKOL HCO-40 | 860.0 mg |
| Butylhydroxytoluene (BHT) | 1.0 mg |
| Formulation Example C: | |
| Product of Ex. 2 | 25.0 mg |
| GLYCOFUROL 75 | 100.0 mg |
| MIGLYOL 812 | 35.0 mg |
| CREMOPHOR RH 40 | 90.0 mg |
| Butylhydroxyanisole (BHA) | 0.2 mg |
| Formulation Example D: | |
| Product of Ex. 2 | 10.0 mg |
| Tetraglycol | 10.0 mg |
| MYRITOL | 5.0 mg |
| CREMOPHOR RH 40 | 75.0 mg |
| alpha-Tocopherol | 0.1 mg |

The individual components of these formulations, as well as the methods for their preparation, are fully described in British Patent Application 2 222 770, the contents of which are incorporated herein by reference.

Determined ED values in the above described Test Methods 1 to 4 for the cyclosporin of Example 2 are as follows:

| TEST METHOD | ED mg/kg | = Dosage required ... |
|---|---|---|
| 1 | 25 (ED50) | to reduce average difference in weight between node pairs by 50% as compared with untreated controls. |
| 2 | 2.5 | to prolong survival to >100 days in 100% of treated rats. |
| 3 | 25 | to reduce disease symptomatology by 100% as compared with untreated controls. |
| 4 | 20 | to reduce swelling to that recorded for untreated controls. |

In accordance with the foregoing the present invention also provides in a further series of embodiments:

A. A method of effecting immunosuppression in a subject in need of such treatment which method comprises administering to said subject an effective amount of a Product Cyclosporin.

B. A method:
1) for the prevention of organ transplant rejection, for example for the treatment of recipients of organ transplants of any of the particular types listed above; or
2) for the prevention of graft-versus-host disease, for example in recipients of bone marrow transplants; or
3) for the treatment of autoimmune disease or for the treatment of inflammatory conditions, for example for the treatment of any such disease or condition listed above; or
4) for the treatment of alopecia or for the promotion of hair growth; or
5) for the treatment of parasitic infection or invasion, for example, for the treatment of protozoal, fungal or vermicular infection or invasion, e.g. for the treatment of coccidiomycosis or malaria; or
6) for the reversal of reduced resistance of malignancies to chemotherapy, for the enhancement of wound healing or for the treatment of asthma;

in a subject in need of such treatment, which method comprises administering to said subject an effective amount of a Product Cyclosporin.

C. A Product Cyclosporin for use as a pharmaceutical, e.g. for use as an immunosuppressant or for use in the treatment of any disease or condition as set forth under B above.

D. A pharmaceutical composition comprising a Product Cyclosporin in association with a pharmaceutically acceptable diluent or carrier.

I claim:

1. A cyclosporin of formula II

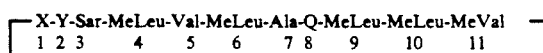

in which
X is MeBmt or dihydro-MeBmt,
Y is αAbu, Val, Thr, or Nva and
Q is a residue of formula I

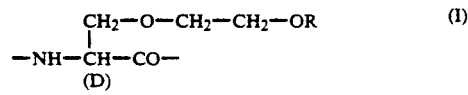

wherein R is hydrogen or a physiologically hydrolysable and acceptable acyl residue.

2. A cyclosporin according to claim 1 in which R is hydrogen.

3. A cyclosporin according to claim 1 in which R is acetyl.

4. A cyclosporin according to claim 1 in which R is ($C_{1-4}$alkyl)carbonyl.

5. [O-(2-Hydroxyethyl)(D)Ser]$^8$-Ciclosporin.

6. [O-(2-Acetyloxyethyl)(D)Ser]$^8$-Ciclosporin.

7. A pharmaceutical composition comprising a therapeutically effective amount of a compound according to claim 1 and a pharmaceutically acceptable carrier therefor.

8. A method of inducing immunosuppression in a subject in need of said treatment, which comprises administering to the subject an immunosuppression effective amount of a compound according to claim 1.

9. A method of preventing organ transplant rejection or graft-versus-host disease, or treating autoimmune disease or inflammatory conditions in a subject in need of said treatment, which comprises administering to the subject a therapeutically effective amount of a compound according to claim 1.

10. A method according to claim 9 of preventing organ transplant rejection.

11. A method according to claim 9 in which the autoimmune disease or inflammatory condition is psoriasis.

12. A method according to claim 9 in which the autoimmune disease or inflammatory condition is rheumatoid arthritis.

* * * * *